(12) United States Patent
Lee et al.

(10) Patent No.: US 8,828,644 B2
(45) Date of Patent: Sep. 9, 2014

(54) COMPOUND, PHOTOSENSITIVE COMPOSITION COMPRISING THE SAME AND PHOTOSENSITIVE MATERIAL

(71) Applicant: LG Chem, Ltd., Seoul (KR)

(72) Inventors: Keon Woo Lee, Daejeon (KR); Sang Kyu Kwak, Daejeon (KR); Changsoon Lee, Daejeon (KR); Hyehyeon Kim, Seoul (KR); Saehee Kim, Seoul (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/009,031

(22) PCT Filed: Jan. 24, 2013

(86) PCT No.: PCT/KR2013/000567
§ 371 (c)(1),
(2), (4) Date: Sep. 30, 2013

(87) PCT Pub. No.: WO2013/115521
PCT Pub. Date: Aug. 8, 2013

(65) Prior Publication Data
US 2014/0065543 A1     Mar. 6, 2014

(30) Foreign Application Priority Data

Feb. 1, 2012 (KR) .......... 10-2012-0010345

(51) Int. Cl.
*C07D 403/02* (2006.01)
*G03F 7/004* (2006.01)
*G03F 7/027* (2006.01)
*C07D 487/04* (2006.01)
*C07C 275/00* (2006.01)

(52) U.S. Cl.
CPC .............. *G03F 7/004* (2013.01); *C07C 275/00* (2013.01); *C07D 487/04* (2013.01); *G03F 7/027* (2013.01); *Y10S 430/128* (2013.01)
USPC ...................... 430/270.1; 430/281.1; 430/927; 548/303.4

(58) Field of Classification Search
CPC ..... C07C 273/00; C07C 275/00; G03F 7/004; G03F 7/027; G03F 7/028
USPC .................. 430/270.1, 281.1, 927; 548/303.4
See application file for complete search history.

(56) References Cited

U.S. PATENT DOCUMENTS 5,055,113 A * 10/1991 Larson et al. .................. 51/298
2012/0007200 A1 1/2012 Lee et al.

FOREIGN PATENT DOCUMENTS

JP     2004-117876 A     4/2004
JP     2009-244780 A     10/2009

* cited by examiner

*Primary Examiner* — Anca Eoff
(74) *Attorney, Agent, or Firm* — Rothwell, Figg, Ernst & Manbeck, P.C.

(57) ABSTRACT

The present application relates to a novel compound, a photosensitive composition comprising the same and a photosensitive material.

20 Claims, 7 Drawing Sheets

COMPOUND, PHOTOSENSITIVE COMPOSITION COMPRISING THE SAME AND PHOTOSENSITIVE MATERIAL

TECHNICAL FIELD

The present application is a 35 U.S.C. §371 National Phase Entry Application from PCT/KR 2013/000567 filed Jan. 24, 2013, and designating the United States, which claims priority to and the benefit of Korean Patent Application No. 10-2012-0010345, filed in the Korean Intellectual Property Office on Feb. 1, 2012, the entire contents of which are incorporated herein by reference.

The present application relates to a new compound, a photosensitive composition comprising the same, and a photosensitive material. More particularly, the present application relates to a crosslinkable compound that may be used in a photosensitive composition, a composition comprising the same, and a photosensitive material.

BACKGROUND ART

A photosensitive composition may be used for curing a dielectric film or a passivation material and the like of a liquid crystal display (LCD). The photosensitive composition may be applied on a substrate to form a coating film and the coating film is entirely exposed to form an insulating film or a protective film, or may be used to form a pattern by performing exposure by light irradiation using a photomask and the like on a specific portion of the coating film, and then removing an exposed portion or non-exposed portion by developing treatment.

The photosensitive composition may be polymerized and cured by irradiating light and thus has been used for photocurable inks, photosensitive printing plates, various photoresists, color filter photoresists for LCDs, photoresists for a resin black matrix, or transparent photosensitive materials or the like.

Among them, the transparent photosensitive composition may be used to form a column spacer, an overcoat or a passivation film. The transparent photosensitive composition typically does not use coloring preparations such as pigments, and may be a liquid-state composition comprising an alkali soluble resin, a polymerizable compound having an ethylenically unsaturated bond, a photopolymerization initiator and a solvent. As the use of LCDs becomes high-quality and diversified, LCDs are being manufactured for the use of constituting liquid crystal display devices, such as TVs, monitors and the like in addition to the use of laptop computers, mobile phones and the like.

Recently, in order to enhance the brightness efficiency of LCDs, a case in which a TFT structure with increased apertures is applied has been increased. Thus, an organic thin film having excellent transmittance for light has been widely used as an insulating film.

Holes with a certain size may be formed in an organic thin film used in this case, in order to enable a gate line or a storage capacitor of a TFT to be connected to a pixel electrode.

In a method for forming holes, a positive-type photosensitive composition is advantageous, but there are problems such as a decrease in transmittance by a photoacid generator (PAG), heat resistance or the like.

DISCLOSURE

Technical Problem

In order to solve the above-described problem in the related art, there is a need for developing a material for a photosensitive composition that may improve characteristics of a film or a pattern or provide excellent effects on the process.

Technical Solution

An exemplary embodiment of the present application provides a compound represented by the following Formula 1.

[Formula 1]

In Formula 1,
at least one of X1 to X4 is the following Formula 2, and the others are hydrogen.

[Formula 2]

in Formula 2,
R1 is an alkylene group having 1 to 6 carbon atoms,
R2 is hydrogen or an alkyl group having 1 to 6 carbon atoms, and
Z1 is a straight or branched alkylene group having 1 to 6 carbon atoms; or a cyclic alkylene group having 3 to 20 carbon atoms.

Another exemplary embodiment of the present application provides a photosensitive composition comprising: a) a crosslinkable compound comprising a compound represented by Formula 1, b) an alkali soluble binder resin, c) a photopolymerization initiator, and d) a solvent.

In addition, the present application provides a photosensitive material prepared by using the photosensitive composition.

Advantageous Effects

The compound according to an exemplary embodiment of the present application is a glycoluril derivative containing an acrylate group, and may serve as the crosslinkable compound in the photosensitive composition. When the photosensitive composition comprising the compound according to an exemplary embodiment of the present application is used, a reverse taper or peeling phenomenon may be minimized to prepare a negative-type thin film which is advantageous in forming holes whose perimeter is clean without scum. The photosensitive composition is advantageous in curing a dielectric film or a passivation material and the like of a liquid crystal display (LCD).

MODE FOR INVENTION

Hereinafter, the present application will be described in more detail.

An exemplary embodiment of the present application provides a new compound represented by Formula 1.

In the specification, means a connection site in the compound.

In Formula 1, at least one of X1 to X4 is Formula 2, and the others are hydrogen.

In Formula 2, R1 is an alkylene group having 1 to 6 carbon atoms and R2 is hydrogen or an alkyl group having 1 to 6 carbon atoms, and Z1 is a straight or branched alkylene group having 1 to 6 carbon atoms; or a cyclic alkylene group having 3 to 20 carbon atoms. Specifically, Z1 may be represented by the following Formula 3 or 4.

[Formula 3]

[Formula 4]

In an exemplary embodiment of this application, Formula 2 may be specifically represented by the following Formula 5 or 6.

[Formula 5]

[Formula 6]

In an exemplary embodiment of this application, at least one of X1 to X4 is the following Formula 5 or 6, and the others may be hydrogen.

One of X1 to X4 is Formula 5 and the other three may be hydrogen, and two of X1 to X4 are Formula 5 and the other two may be hydrogen. Furthermore, three of X1 to X4 are Formula 5 and the other one may be hydrogen, and all of X1 to X4 may be Formula 2.

In addition, one of X1 to X4 is Formula 6 and the other three may be hydrogen, and two of X1 to X4 are Formula 6 and the other two may be hydrogen. Furthermore, three of X1 to X4 are Formula 6 and the other one may be hydrogen, and all of X1 to X4 may be Formula 3.

Further, two of X1 to X4 are Formulas 5 and 6 and the other two may be hydrogen, three of X1 to X4 are one Formula 5 and two of Formula 6 and the other one may be hydrogen, and three of X1 to X4 are two of Formula 5 and one Formula 6 and the other one may be hydrogen. In addition, all of X1 to X4 may be n (n is an integer from 1 to 3) of Formula 5 and (4−n) of Formula 6.

In an exemplary embodiment of this application, Formula 6 may be represented by the following Formula 7 or 8.

[Formula 7]

[Formula 8]

In Formulas 5 to 8, R3, R5, R7 and R9 are the same as or different from each other, and each independently an alkylene group having 1 to 6 carbon atoms. Specifically, all of R3, R5, R7 and R9 may be a methylene group.

R4, R6, and R8 and R10 are the same as or different from each other, and each hydrogen or an alkyl group having 1 to 6 carbon atoms. Specifically, R4, R6, and R8 and R10 are the same as or different from each other, and may be each hydrogen or a methyl group.

In an exemplary embodiment of this application, Formula 1 may be represented by the following Formula 9.

[Formula 9]

In Formula 9, Z1 to Z4 are the same as or different from each other, and may be each independently represented by Formula 3 or 4.

In an exemplary embodiment of this application, Formula 1 may be represented by the following Formula 10.

[Formula 10]

In Formula 9 or 10, A1 to A4 are the same as or different from each other, and each independently an alkylene group having 1 to 6 carbon atoms. Specifically, all of A1 to A4 may be a methylene group.

In Formula 9 or 10, A5 to A8 are the same as or different from each other, and each hydrogen or an alkyl group having 1 to 6 carbon atoms. Specifically, A5 to A8 are the same as or different from each other, and may be each hydrogen or a methyl group.

In the compound according to an exemplary embodiment of this application, the substituents of the above Formulas will be described in more detail as follows.

The alkyl group may be a straight or branched chain having 1 to 6 carbon atoms. The branched alkyl group may be a branched alkyl group having 2 to 6 carbon atoms.

Specific examples thereof include a methyl group, an ethyl group, a propyl group, an isopropyl group, a butyl group, a t-butyl group, a pentyl group, a hexyl group or the like, but are not limited thereto.

When the alkyl group is a cyclic alkylene group, the alkyl group may be a cyclic alkylene group having 3 to 20 carbon atoms, and may be specifically a cyclic alkylene group having 3 to 10 carbon atoms or 3 to 6 carbon atoms. Specific examples thereof include a cyclopropyl group, a cyclobutyl group, a cyclopentyl group, a cyclohexyl group or the like, but are not limited thereto.

The alkylene group is a case in which the alkyl group is used as a divalent substituent.

Furthermore, an exemplary embodiment of the present application provides a photosensitive composition comprising: a) a crosslinkable compound comprising the compound represented by Formula 1, b) an alkali soluble binder resin, c) a photopolymerization initiator, and d) a solvent.

Only one kind of compound represented by Formula 1 may be included in the photosensitive composition, and two or more kinds thereof may also be mixed and included in the photosensitive composition. Specifically, the compound represented by Formula 1 may be a mixture of two or more compounds in which the substituents of X1 to X4 are the same as each other, and may be a mixture of two or more compounds in which the substituents of X1 to X4 are different from each other. For example, the compound may be a mixture of two or more of a compound in which at least one of X1 to X4 is Formula 5, a compound in which at least one of X1 to X4 is Formula 6 and a compound in which at least two of X1 to X4 are Formulas 5 and 6.

The compound represented by Formula 1 may be specifically the compound represented by Formula 9. The compound represented by Formula 1 may be specifically the compound represented by Formula 10.

In a negative-type photosensitive composition, a region exposed to light such as UV rays responds to light and then remains after a development process and thus when holes are formed, it may be difficult to form normal holes due to the diffraction phenomenon around the light blocking region of a photomask.

When the acid value of the material is increased or the molecular weight of the binder polymer is decreased in order to overcome the problem, the developing solution penetrates through the interface of holes to generate reverse tapers, or when the phenomenon becomes more severe, the thin film may be peeled off in some cases.

At this time, when the thin film is subjected to sintering process (hard bake), a flow of polymer caused by heat may occur in a region in which a reverse taper is generated, thereby causing a drawback that the shape of holes are not maintained constantly.

The present inventors have noted that there are the aforementioned problems, have conducted intensive studies, and as a result, have found that an excellent effect may be produced by comprising the compound represented by Formula as a crosslinkable compound in the photosensitive composition.

In the photosensitive composition according to an exemplary embodiment of this application, a) the compound represented by Formula 1 may be comprised in an amount of 5 wt % or more based on the total weight of the solid except for the solvent. When the compound is comprised in an amount less than 5 wt %, an effect to be obtained in the present application may not be secured.

The photosensitive composition may use the compound represented by Formula 1 as a crosslinkable compound alone, and may also additionally comprise another crosslinkable compound containing two or more unsaturated groups.

The crosslinkable compound that may be additionally used is not particularly limited, but it is possible to use a compound comprising two or more ethylenically unsaturated groups, for example, two or more acryl groups. Specific examples of the crosslinkable compound may be selected from the group consisting of compounds obtained by esterifying a polyhydric alcohol, such as ethylene glycol di(meth)acrylate, polyethylene glycol di(meth)acrylate having 2 to 14 ethylene groups, trimethylolpropane di(meth)acrylate, trimethylolpropane tri(meth)acrylate, pentaerythritol tri(meth)acrylate, pentaerythritol tetra(meth)acrylate, 2-trisacryloyloxymethylethylphthalic acid, propylene glycol di(meth)acrylate having 2 to 14 propylene groups, dipentaerythritol penta(meth)acrylate, dipentaerythritol hexa(meth)acrylate, a mixture of an acid modified product of dipentaerythritol penta(meth)acrylate and dipentaerythritol hexa(meth)acrylate (trade name: TO-2348 and TO-2349 manufactured by Japanese Toagosei Co., Ltd.) and the like, with α,β-unsaturated carboxylic acids; compounds obtained by adding (meth)acrylic acids to a glycidyl group-containing compound such as a trimethylolpropane triglycidyletheracrylic acid adduct, a bisphenol A diglycidyletheracrylic acid adduct and the like; ester compounds obtained from a polyhydric carboxylic acid and a compound having a hydroxyl group or an ethylenically unsaturated bond, or polyisocyanate adducts of compounds having a hydroxyl group or an ethylenically unsaturated bond, such as phthalic acid diester of β-hydroxyethyl(meth)acrylate, a toluene diisocyannate adduct of β-hydroxyethyl (meth)acrylate, and the like, or adducts with polyisocyanate; (meth)acrylic acid alkyl esters such as methyl (meth)acrylate, ethyl (meth)acrylate, butyl (meth)acrylate, 2-ethylhexyl (meth)acrylate and the like; and 9,9'-bis[4-(2-acryloyloxyethoxy)phenyl]fluorene, but the range of the present application is not limited thereto and those known in the art may be used. The above-described examples may be used either alone or in a mixture of two or more thereof.

Further, in some cases, a silica dispersion may be used in addition to the above-described crosslinkable compound. Examples of the silica dispersion include Nanocryl XP series (0596, 1045 and 21/1364) and Nanopox XP series (0516 and 0525), manufactured by Hanse Chemie Co., Ltd., and the like.

It is preferred that a) the crosslinkable compound comprising the compound represented by Formula 1 is comprised in an amount from 1 part by weight to 30 parts by weight based on 100 parts by weight of the entire composition. When the content of the crosslinkable compound is 1 part by weight or more, a crosslinking reaction by light may be advantageously performed. When the content of the crosslinkable compound is 30 parts by weight or less, the solubility with respect to the alkali is not inhibited, which is advantageous in forming a pattern.

In the photosensitive composition according to an exemplary embodiment of this application, a binder resin having a weight average molecular weight from 3,000 to 150,000 may be used as b) the alkali soluble binder resin. When the weight average molecular weight of the alkali soluble binder resin is 3,000 or more, heat resistance and chemical resistance are maintained, and when the weight average molecular weight thereof is 150,000 or less, development may be performed while the resin has solubility with respect to a developing solution, which is equal to or more than a predetermined value, and it is possible to uniformly apply the resulting solution because the viscosity of the solution may be maintained.

An alkali soluble binder resin having an acid value from 30 KOH mg/g to 300 KOH mg/g may be used as the alkali soluble binder resin. When the acid value is 30 KOH mg/g or more, development is performed well to obtain clean patterns, and when the acid value is 300 KOH mg/g or less, a washing characteristic is excessively improved to prevent patterns from being fallen off.

It is preferred that b) the alkali soluble binder resin is comprised in an amount from 1 part by weight to 20 parts by weight based on 100 parts by weight of the entire composition. When the content of the alkali soluble resin is 1 part by weight or more, solubility with respect to the developing solution appears, and thus it is proper to form a pattern, and when the content thereof is 20 parts by weight or less, the viscosity of the entire solution is in a predetermined level or less, which is advantageous in coating the composition.

In the photosensitive composition according to an exemplary embodiment of this application, c) the photopolymerization initiator is not particularly limited, but it is possible to use one or more selected from the group consisting of triazine-based compounds; biimidazole compounds; acetophenone-based compounds; O-acyloxime-based compounds; benzophenone-based compounds; tioxanthone-based compounds; phosphine oxide-based compound; and coumarin-based compounds.

Non-limiting examples of the photopolymerization initiator include a triazine-based compound, such as 2,4-trichloromethyl-(4'-methoxyphenyl)-6-triazine, 2,4-trichloromethyl-(4'-methoxystyryl)-6-triazine, 2,4-trichloromethyl-(fipronil)-6-triazine, 2,4-trichloromethyl-(3',4'-dimethoxyphenyl)-6-triazine, 3-{4-[2,4-bis(trichloromethyl)-s-triazine-6-yl]phenylthio}propanoic acid, 2,4-trichloromethyl-(4'-ethylbiphenyl)-6-triazine, 2,4-trichloromethyl-(4'-methylbiphenyl)-6-triazine and the like; a biimidazole compound, such as 2,2'-bis(2-chlorophenyl)-4,4',5,5'-tetraphenyl biimidazole, 2,2-bis(2,3-dichlorophenyl)-4,4',5,5'-tetraphenyl biimidazole and the like; an acetophenone-based compound such as 2-hydroxy-2-methyl-1-phenylpropan-1-one, 1-(4-isopropylphenyl)-2-hydroxy-2-methylpropan-1-one, 4-(2-hydroxyethoxy)-phenyl (2-hydroxy)propyl ketone, 1-hydroxycyclohexyl phenyl ketone, 2,2-dimethoxy 2-phenyl acetophenone, 2-methyl-(4-methylthiophenyl)-2-morpholino-1-propan-1-one (Irgacure-907), 2-benzyl-2-dimethylamino-1-(4-morpholinophenyl)-butan-1-one (Irgacure-369) and the like; an O-acyloxime based compound, such as Irgacure OXE 01 and Irgacure OXE 02, manufactured by CIBA Geigy Corp.; a benzophenone-based compound, such as 4,4'-bis(dimethylamino)benzophenone 4,4'-bis(diethylamino)benzophenone and the like; a tioxanthone-based compound, such as 2,4-diethyl tioxanthone, 2-chloro tioxanthone, isopropyl tioxanthone, diisopropyl tioxanthone and the like; a phosphine oxide-based compound, such as 2,4,6-trimethylbenzoyl diphenylphosphine oxide, bis(2,6-dimethoxybenzoyl)-2,4,4-trimethylpentyl phosphine oxide, bis(2,6-dichlorobenzoyl) propyl phosphine oxide and the like; a coumarin-based compound, such as 3,3'-carbonylvinyl-7-(diethylamino)coumarin, 3-(2-benzothiazolyl)-7-(diethylamino) coumarin, 3-benzoyl-7-(diethylamino) coumarin, 3-benzoyl-7-methoxy-coumarin, and 10,10'-carbonylbis[1,1,7,7-tetramethyl-2,3,6,7-tetrahydro-1H,5H,11H—Cl]-benzopyrano[6,7,8-ij]-quinolizin-11-one; and the like. Among them, it is possible to mix one or two or more and use the mixture.

It is preferred that c) the photopolymerization initiator is comprised in an amount from 0.1 part by weight to 5 parts by weight based on 100 parts by weight of the entire composition. When the content of the photopolymerization initiator is 0.1 part by weight or more, sufficient sensitivity may be obtained, and when the content thereof is 5 parts by weight or less, UV light may be transferred up to the bottom by controlling the UV absorbance.

In the photosensitive composition according to an exemplary embodiment of this application, non-limiting examples of d) the solvent include one or more selected from the group consisting of methyl ethyl ketone, methyl cellosolve, ethyl cellosolve, ethylene glycol dimethyl ether, ethylene glycol diethyl ether, propylene glylcol dimethyl ether, propylene glylcol diethyl ether, diethylene glycol dimethyl ether, diethylene glycol diethyl ether, diethylene glycol methyl ethyl ether, 2-ethoxy propanol, 2-methoxy propanol, 3-methoxy butanol, cyclohexanone, cyclopentanone, propylene glylcol methyl ether acetate, propylene glylcol ethyl ether acetate, 3-methoxybutyl acetate, ethyl 3-ethoxypropionate, ethyl cellosolve acetate, methyl cellosolve acetate, butyl acetate and dipropylene glylcol monomethyl ether, but are not limited thereto.

It is preferred that d) the solvent is comprised in an amount from 50 parts by weight to 95 parts by weight based on 100 parts by weight of the entire composition.

The photosensitive composition according to an exemplary embodiment of the present application may comprise a) the crosslinkable compound comprising the compound of claim 1 in an amount from 1 part by weight to 30 parts by weight, b) the alkali soluble binder resin in an amount from 1 part by weight to 20 parts by weight, c) the photopolymerization initiator in an amount from 0.1 part by weight to 5 parts by weight, and d) the solvent in an amount from 50 parts by weight to 95 parts by weight, based on 100 parts by weight of the entire composition.

The photosensitive composition according to an exemplary embodiment of the present application may additionally include, if necessary, one or more selected from a colorant, a curing accelerator, a thermal polymerization inhibitor, a plasticizer, an adhesive accelerator, a filler and a surfactant, in addition to the constituent components.

As the colorant, one or more pigments, dyes or mixtures thereof may be used. Specific examples of black pigments include metal oxides, such as carbon black, graphite, titan black and the like. Examples of carbon black include SEAST 5HIISAF-HS, SEAST KH, SEAST 3HHAF-HS, SEAST NH, SEAST 3M, SEAST 300HAF-LS, SEAST 116HMMAF-HS, SEAST 116MAF, SEAST FMFEF-HS, SEAST SOFEF, SEAST VGPF, SEAST SVHSRF-HS and SEAST SSRF (Tokai Carbon Co., Ltd); DIAGRAM BLACK II, DIAGRAM BLACK N339, DIAGRAM BLACK SH, DIAGRAM BLACK H, DIAGRAM LH, DIAGRAM HA, DIAGRAM SF, DIAGRAM N550M, DIAGRAM M, DIAGRAM E, DIAGRAM G, DIAGRAM R, DIAGRAM N760M, DIAGRAM LR, #2700, #2600, #2400, #2350, #2300, #2200, #1000, #980, #900, MCF88, #52, #50, #47, #45, #45L, #25, #CF9, #95, #3030, #3050, MA7, MA77, MA8, MA11, MA100, MA40, OIL7B, OIL9B, OIL11B, OIL30B and OIL31B (Mitsubishi Chemical Corporation); PRINTEX-U, PRINTEX-V, PRINTEX-140U, PRINTEX-140V, PRINTEX-95, PRINTEX-85, PRINTEX-75, PRINTEX-55, PRINTEX-45, PRINTEX-300, PRINTEX-35, PRINTEX-25, PRINTEX-200, PRINTEX-40, PRINTEX-30, PRINTEX-3, PRINTEX-A, SPECIAL BLACK-550, SPECIAL BLACK-350, SPECIAL BLACK-250, SPECIAL BLACK-100 and LAMP BLACK-101 (Degussa Co., Ltd.); RAVEN-1100ULTRA, RAVEN-1080ULTRA, RAVEN-1060ULTRA, RAVEN-1040, RAVEN-1035, RAVEN-1020, RAVEN-1000, RAVEN-890E, RAVEN-890, RAVEN-880ULTRA, RAVEN-860ULTRA, RAVEN-850, RAVEN-820, RAVEN-790ULTRA, RAVEN-780ULTRA, RAVEN-760ULTRA, RAVEN-520, RAVEN-500, RAVEN-460, RAVEN-450, RAVEN-430ULTRA, RAVEN-420, RAVEN-410, RAVEN-2500ULTRA, RAVEN-2000, RAVEN-1500, RAVEN-1255, RAVEN-1250, RAVEN-1200, RAVEN-1190ULTRA, RAVEN-1170 (Columbia Carbon Co., Ltd.), mixtures thereof, or the like. In addition, examples of a colored colorant include Carmine 6B (C.I. 12490), Phthalocyanine Green (C.I. 74260), Phthalocyanine Blue (C.I. 74160), Perylene Black (BASF K0084 and K0086), Cyanine Black, Lionol Yellow (C.I. 21090), Lionol Yellow GRO (C.I. 21090), Benzidine Yellow 4T-564D, Victoria Pure Blue (C.I. 42595), C.I. PIGMENT RED 3, 23, 97, 108, 122, 139, 140, 141, 142, 143, 144, 149, 166, 168, 175, 177, 180, 185, 189, 190, 192, 202, 214, 215, 220, 221, 224, 230, 235, 242, 254, 255, 260, 262, 264 and 272; C.I. PIGMENT GREEN 7 and 36; C.I. PIGMENT BLUE 15:1, 15:3, 15:4, 15:6, 16, 22, 28, 36, 60 and 64; C.I. PIGMENT YELLOW 13, 14, 35, 53, 83, 93, 95, 110, 120, 138, 139, 150, 151, 154, 175, 180, 181, 185, 194 and 213; and C.I. PIGMENT VIOLET 15, 19, 23, 29, 32 and 37, and the like, and white and fluorescent pigments and the like may also be used. As a phthalocyanine-based complex compound used as the pigment, it is also possible to use a material that contains zinc as the central metal in addition to copper.

Examples of the curing accelerator include one or more selected from the group consisting of 2-mercaptobenzoimidazole, 2-mercaptobenzothiazole, 2-mercaptobenzooxazole, 2,5-dimercapto-1,3,4-thiadiazole, 2-mercapto-4,6-dimethylaminopyridine, pentaerythritol tetrakis(3-mercaptopropionate), pentaerythritol tris(3-mercaptopropionate), pentaerythritol tetrakis(2-mercaptoacetate), pentaerythritol tris (2-mercaptoacetate), trimethylolpropane tris(2-mercaptoacetate), trimethylolpropane tris(3-mercaptopropionate), trimethylolethane tris(2-mercaptoacetate), and trimethylolethane tris(3-mercaptopropionate), but are not limited thereto and may include those known in the art.

Examples of the thermal polymerization inhibitor include one or more selected from the group consisting of p-anisole, hydroquinone, pyrocatechol, t-butyl catechol, N-nitrosophenylhydroxyamine ammonium salt, N-nitrosophenylhydroxyamine aluminum salt, and phenothiazine, but are not limited thereto and may include those known in the art.

In addition to the constituent components, it is possible to use all the compounds that may be included in the photosensitive composition in the related art, such as a plasticizer, an adhesion promoter, a filler, a surfactant and the like.

When other components are added to the photosensitive composition according to an exemplary embodiment of this application, it is preferred that the colorant and the other additives are comprised in amounts from 1 part by weight to 20 parts by weight and from 0.01 part by weight to 5 parts by weight, respectively, based on 100 parts by weight of the entire composition.

The photosensitive composition according to an exemplary embodiment of the present invention may be used in a roll coater, a curtain coater, a spin coater, a slot die coater, various printings, dipping and the like, and may be applied on a support such as metal, paper, a glass plastic substrate and the like.

Furthermore, the photosensitive composition may be transferred to other supporters after the composition is applied on a support such as a film and the like, or may be transferred to a blanket and the like and transferred to a second support again after the composition is applied on a first support, and there are no particular limitations on the application methods.

Examples of a light source for curing the photosensitive composition according to an exemplary embodiment of the present application include a mercury vapor arc, a carbon arc, a xenon (Xe) arc and the like, which emit light having a wavelength of 250 nm to 450 nm, but are not limited thereto.

Further, the present application provides a photosensitive material prepared by using the photosensitive composition. The photosensitive composition is present in a state in which at least a portion of the solvent is removed or photocured by drying and/or curing the photosensitive material.

The photosensitive material according to an exemplary embodiment of the present application is preferably used in a photoacrylic photosensitive material that serves as a dielectric film when a TFT-LCD or an organic light emitting diode is manufactured, a pigment-dispersion type photosensitive material, a photosensitive material for forming a black matrix, a photosensitive material for forming an overcoat layer or a column spacer photosensitive material, but may also be used in the manufacture of a photocurable paint, a photocurable ink, a photocurable adhesive, a printing plate, a photosensitive material for a printed circuit board, other transparent photosensitive materials, PDP, and the like, and there are no particular limitations on the use thereof.

Hereinafter, preferred Examples will be provided for better understanding of this application. However, the following Examples are provided only for the purpose of understanding the present application more easily, but the present invention is not limited thereby.

In addition, the following Examples illustrate only a portion of the examples according to an exemplary embodiment of this application, but it is obvious to those skilled in the art that substantially the same effect as the present application may be obtained even when equivalents thereof are used.

SYNTHETIC EXAMPLE 1

10 mol of glycoluril (Sigma-Aldrich) was diluted in propylene glycol monomethyl ether acetate. While the solution was maintained at 50° C., a solution obtained by diluting 40 mol of glycidyl acrylate (Sigma-Aldrich) in the same solvent was slowly added thereto to allow the mixture to react. The obtained solution was separated through a column, and then the solvent was removed by using vacuum distillation, thereby obtaining a compound represented by [Formula 11]. The procedure was repeated to prepare a sufficient amount of the compound of [Formula 11].

[Formula 11]

The structure was confirmed through $^1$H-NMR. 5.80, 6.05, 6.43 (—CH=CH$_2$), 3.43, 4.28, 4.43, 4.44 (aliphatic H), 2.0 (—OH)

SYNTHETIC EXAMPLE 2

A compound represented by [Formula 12] was obtained by using the same method as in [Synthetic Example 1] to allow the mixture to react, except that 40 mol of glycidyl methacrylate (Sigma-Aldrich) was used instead of 40 mol of glycidyl acrylate (Sigma-Aldrich).

[Formula 12]

The structure was confirmed through $^1$H-NMR: 1.93 (—CH$_3$), 5.58, 6.15 (>C=CH$_2$), 3.43, 4.28, 4.43, 4.44 (aliphatic H), 2.0 (—OH)

EXAMPLE 1

In order to confirm the effect of this application, the following photosensitive composition was prepared. 12 g of the binder BzMA/MAA (molar ratio: 70/30, Mw: 24,000) composed of an alkali soluble resin, 8 g of the compound of [Formula 11] as a crosslinkable compound, 1 g of Irgacure OXE-02 manufactured by CIBA Geigy Corp. as a photopolymerization initiator, and 83 g of PGMEA as an organic solvent were mixed for 3 hours by using shaker to prepare photosensitive composition solution, and a photosensitive composition was obtained with a 5-lam filter and used.

The photosensitive composition was applied using a spin coating method to form a uniform thin film, and then the solvent was volatilized by performing a prebake process at 100° C. for 200 seconds. The thickness of the dried thin film was about 4.2 μm.

The thin film was exposed under a high pressure mercury lamp by using an independent pattern-type photomask having a diameter which is constituted with a square having the same length and breadth as 10 μm. Subsequently, the thin film was developed in a dipping mode while maintaining the temperature at 23° C. with a TMAH alkali aqueous solution having a pH from 12.5 to 13.7, washed with pure water and dried by air blowing, thereby forming a pattern.

EXAMPLE 2

A process was performed in the same manner as in [Example 1], except that 4 g of the compound of [Formula 11] and 4 g of pentaerythritol hexaacrylate were put thereinto instead of 8 g of the compound of [Formula 11] as the crosslinkable compound in [Example 1].

EXAMPLE 3

A process was performed in the same manner as in [Example 1], except that 1 g of the compound of [Formula 11] and 7 g of pentaerythritol hexaacrylate were put thereinto instead of 8 g of the compound of [Formula 11] as the crosslinkable compound in [Example 1].

EXAMPLE 4

A process was performed in the same manner as in [Example 1], except that 8 g of the compound of [Formula 12] was put thereinto instead of 8 g of the compound of [Formula 11] as the crosslinkable compound in [Example 1].

EXAMPLE 5

A process was performed in the same manner as in [Example 1], except that 4 g of the compound of [Formula 12] and 4 g of pentaerythritol hexaacrylate were put thereinto instead of 8 g of the compound of [Formula 11] as the crosslinkable compound in [Example 1].

EXAMPLE 6

A process was performed in the same manner as in [Example 1], except that 1 g of the compound of [Formula 12] and 7 g of pentaerythritol hexaacrylate were put thereinto instead of 8 g of the compound of [Formula 11] as the crosslinkable compound in [Example 1].

COMPARATIVE EXAMPLE

A process was performed in the same manner as in [Example 1], except that 8 g of pentaerythritol hexaacrylate was put thereinto instead of 8 g of the compound of [Formula 11] as the crosslinkable compound in [example 1].

EXPERIMENTAL EXAMPLE 1

Whether Scum is Generated

Figure 1:
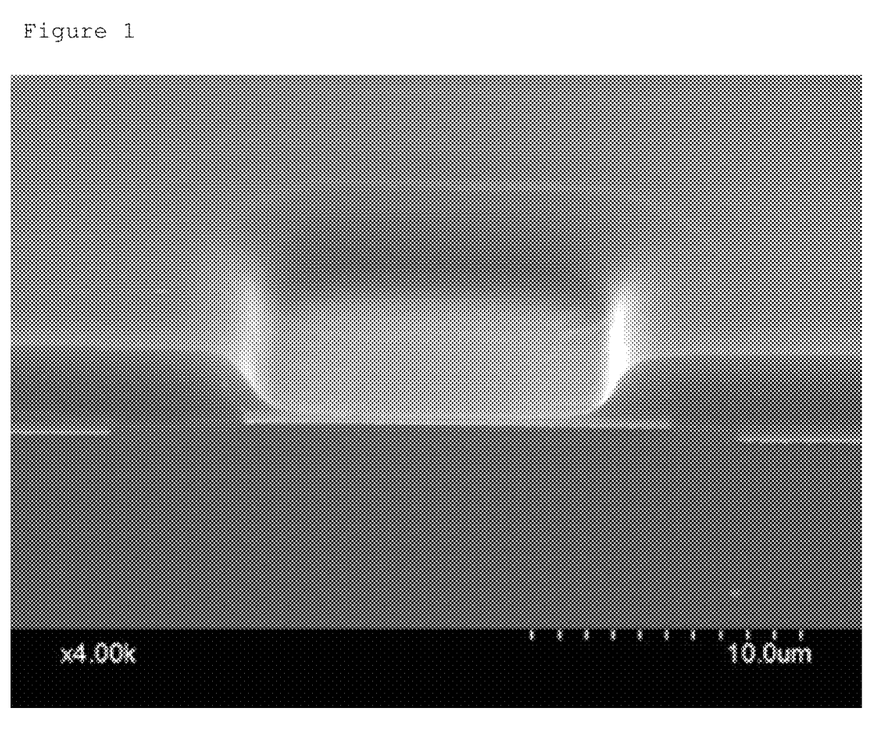
FIG. 1 is a view illustrating the observation of a hole pattern formed by using a photosensitive composition in Example 1 through a scanning electron microscope (SEM).
Figure 2:
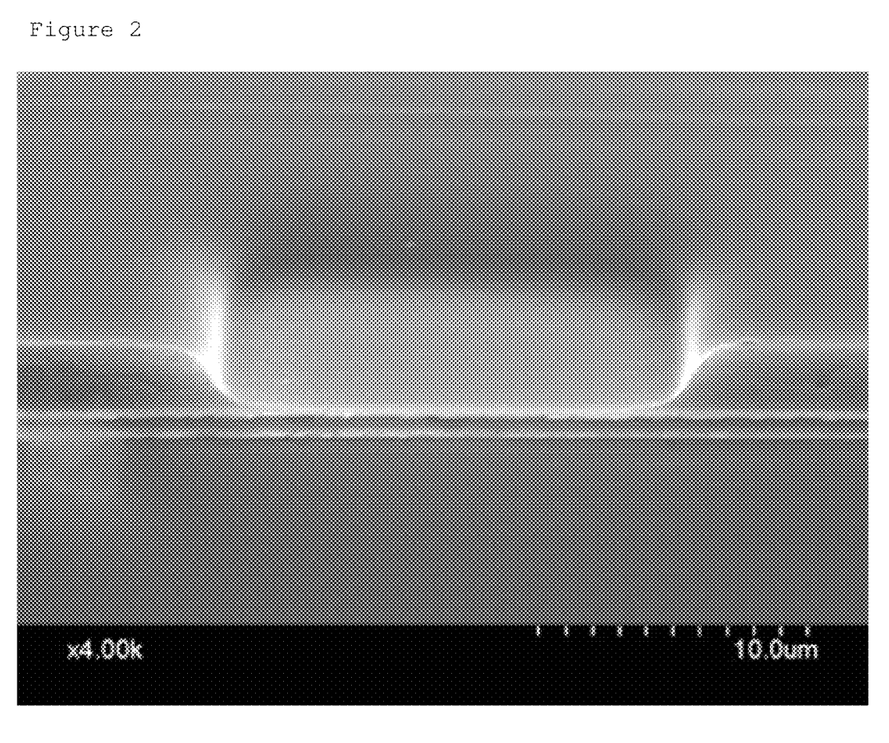
FIG. 2 is a view illustrating the observation of a hole pattern formed by using a photosensitive composition in Example 2 through a scanning electron microscope (SEM).
Figure 3:
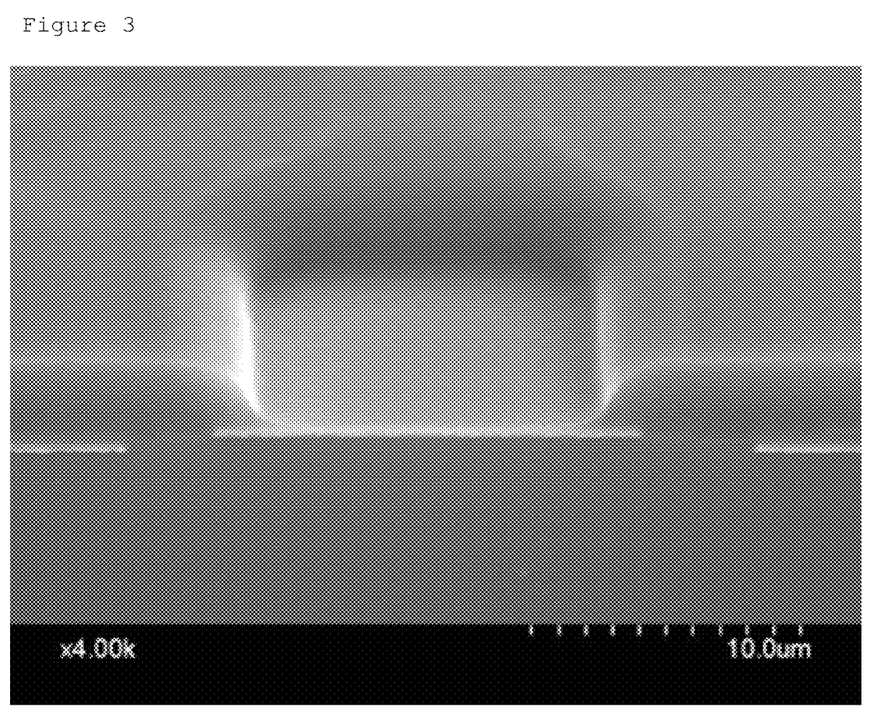
FIG. 3 is a view illustrating the observation of a hole pattern formed by using a photosensitive composition in Example 3 through a scanning electron microscope (SEM).
Figure 4:
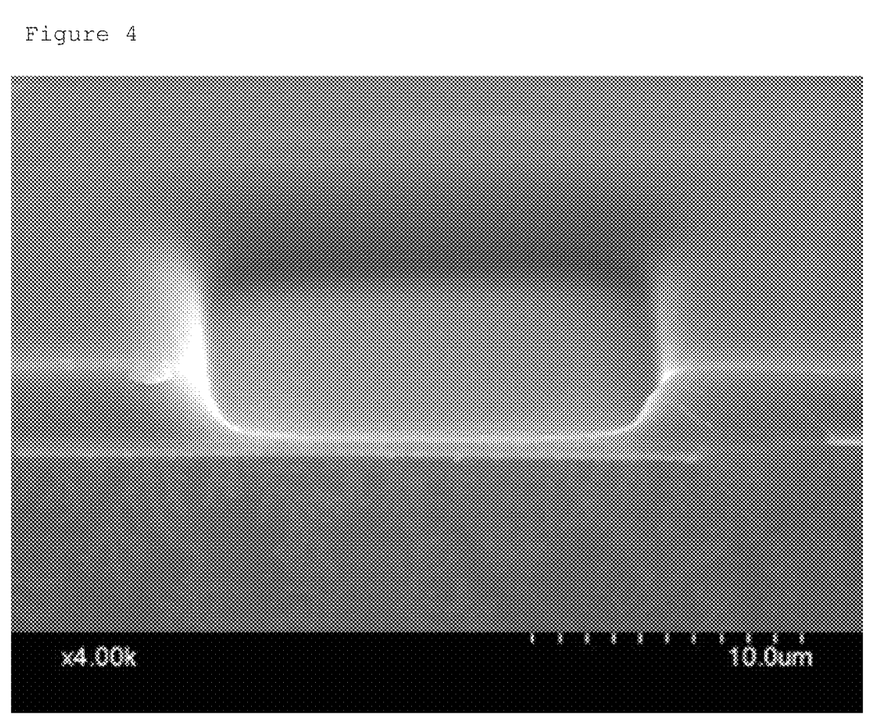
FIG. 4 is a view illustrating the observation of a hole pattern formed by using a photosensitive composition in Example 4 through a scanning electron microscope (SEM).
Figure 5:
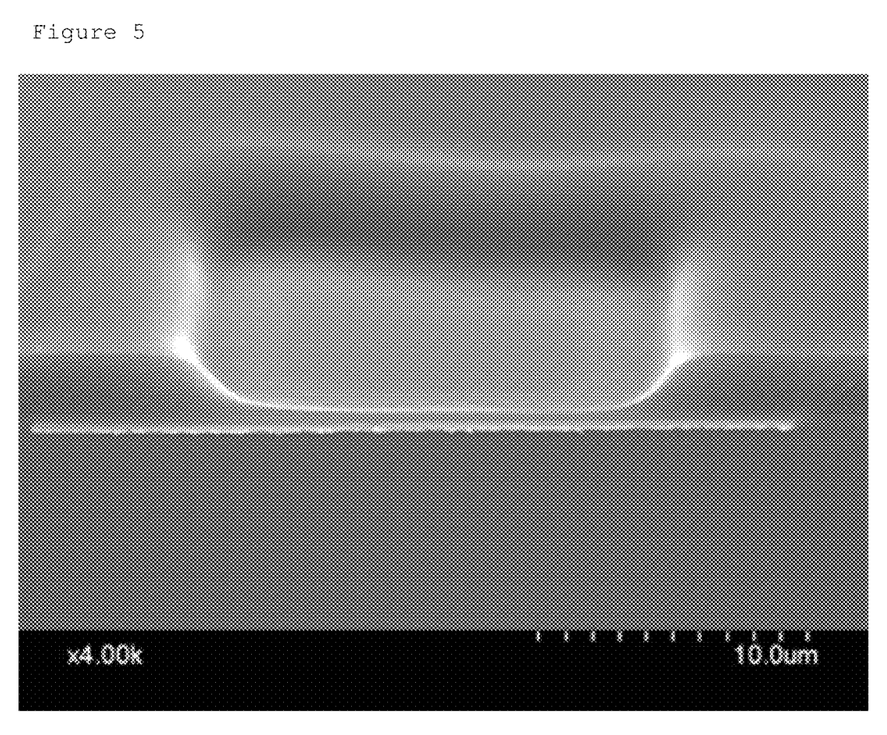
FIG. 5 is a view illustrating the observation of a hole pattern formed by using a photosensitive composition in Example 5 through a scanning electron microscope (SEM).
Figure 6:
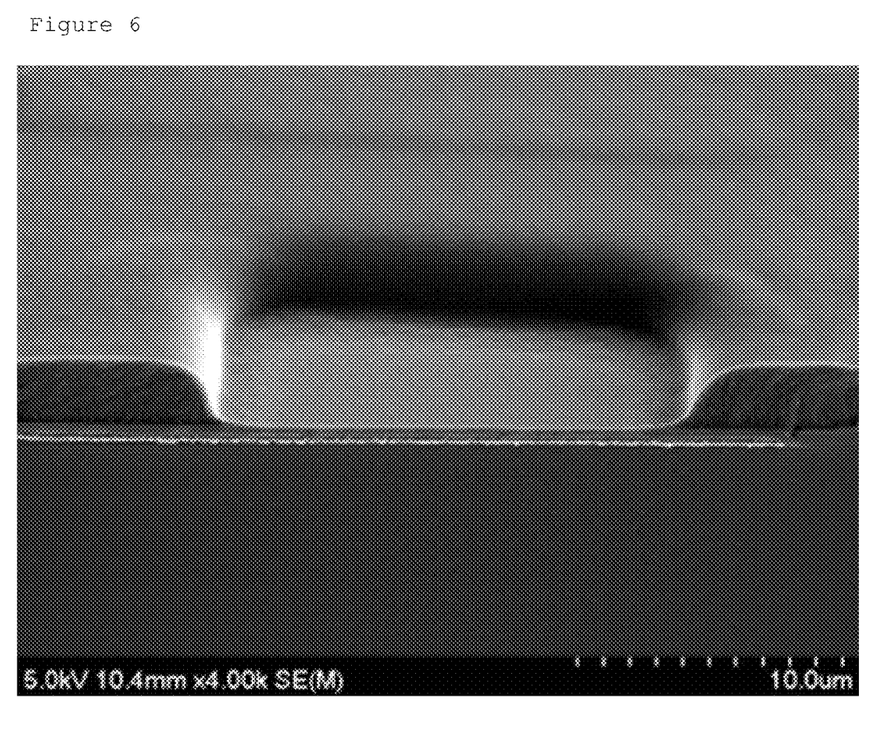
FIG. 6 is a view illustrating the observation of a hole pattern formed by using a photosensitive composition in Example 6 through a scanning electron microscope (SEM).
Figure 7:
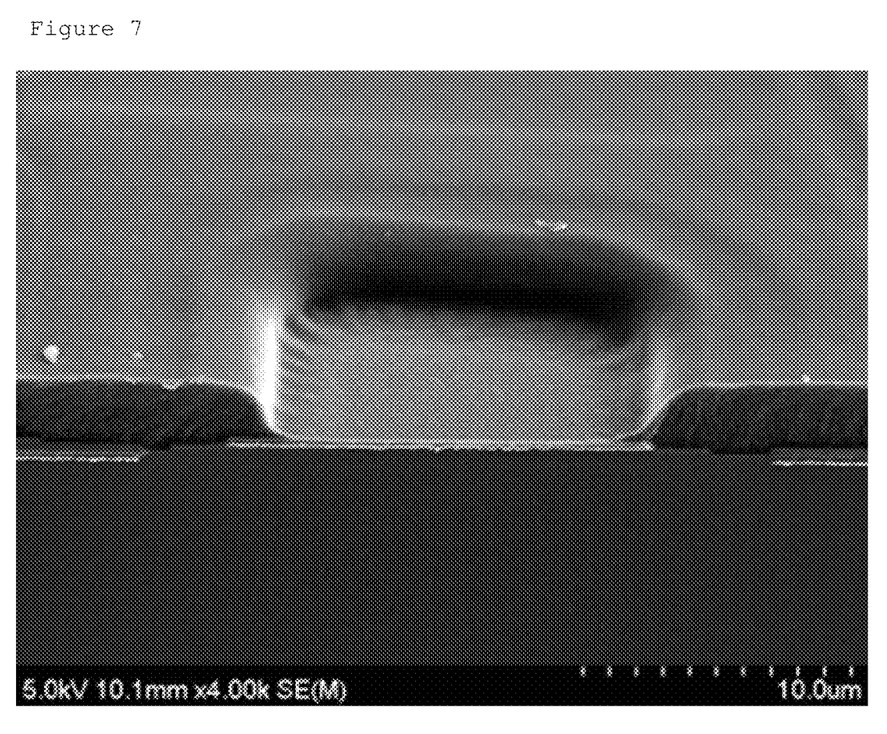
FIG. 7 is a view illustrating the observation of a hole pattern formed by using a photosensitive composition in a Comparative Example through a scanning electron microscope (SEM).

Hole patterns formed by using the photosensitive compositions in Examples 1 to 6 and the Comparative Example were left to stand for 40 minutes in a convection oven maintained at 220° C., and then observed through a scanning electron microscope (SEM) to confirm whether the scum was generated at the end of the taper, and the results are shown in the following [Table 1]. Further, SEM photos of hole patterns according to Examples 1 to 6 and the Comparative Example are illustrated in FIGS. 1 to 7 in order to confirm whether the scum was generated.

EXPERIMENTAL EXAMPLE 2

Measurement of Thin Film Strength

In addition, in order to measure the strength of thin films formed by using the photosensitive compositions in Examples 1 to 6 and the Comparative Example, the thin films were left to stand for 40 minutes in a convection oven maintained at 220° C., and then the strength was measured by using a nanoindenter (Nanoindenter manufactured by MTS Systems Corp.) equipment and a Berkovich tip.

TABLE 1

| Sample | Crosslinkable Compound | | | Whether scum was generated | Thin Film Strength (Gpa) |
| --- | --- | --- | --- | --- | --- |
| | Pentaerythritol hexa-acrylate | [Formula 11] | [Formula 12] | | |
| Example 1 | 0 | 8 | 0 | None | 0.27 |
| Example 2 | 4 | 4 | 0 | None | 0.28 |
| Example 3 | 7 | 1 | 0 | None | 0.28 |
| Example 4 | 0 | 0 | 8 | None | 0.27 |
| Example 5 | 4 | 0 | 4 | None | 0.27 |
| Example 6 | 7 | 0 | 1 | None | 0.28 |
| Comparative Example | 8 | 0 | 0 | Yes | 0.28 |

In Table 1, when hole patterns are formed by using the photosensitive composition comprising the compound according to an exemplary embodiment of the present application in an amount of 1 part by weight or more, it can be known that the generation of scum was significantly decreased and almost no scum was observed.

Furthermore, the thin film strength of formed by using the photosensitive composition is 0.25 Gpa or more, excellent effects may be obtained. When the thin film strength is less than 0.25 Gpa, there is a problem in that the thin film may be damaged during a subsequent process such as rubbing. In Table 1, it can be known that for the thin film strength, all of Examples 1 to 6 and Comparative Example showed values equal to or more than 0.27 Gpa, which are good results. Accordingly, it can be confirmed that excellent effects are shown in thin film strength even in the case of including pentaerythritol hexaacrylate and further including the crosslinkable compound of Formula 11 or 12, and even in the case of only including the crosslinkable compound of Formula 11 or 12.

The invention claimed is:

1. A compound represented by the following Formula 1:

[Formula 1]

in Formula 1,
at least one of X1 to X4 is the following Formula 2, and the others are hydrogen,

[Formula 2]

in Formula 2,
R1 is an alkylene group having 1 to 6 carbon atoms,
R2 is hydrogen or an alkyl group having 1 to 6 carbon atoms, and
Z1 is a straight or branched alkylene group having 1 to 6 carbon atoms; or a cyclic alkylene group having 3 to 20 carbon atoms.

2. The compound according to claim 1, wherein Z1 in Formula 2 is a compound represented by the following Formula 3 or 4:

[Formula 3]

[Formula 4]

3. The compound according to claim 1, wherein Formula 1 is the following Formula 9:

[Formula 9]

in Formula 9,
Z1 to Z4 are the same as or different from each other, and each independently represented by the following Formula 3 or 4,

[Formula 3]

[Formula 4]

A1 to A4 are the same as or different from each other, and each independently an alkylene group having 1 to 6 carbon atoms, and
A5 to A8 are the same as or different from each other, and each hydrogen or an alkyl group having 1 to 6 carbon atoms.

4. The compound according to claim 3, wherein all of A1 to A4 are a methylene group, and A5 to A8 are the same as or different from each other, and each hydrogen or a methyl group.

5. A photosensitive composition comprising:
a) a crosslinkable compound comprising a compound represented by Formula 1 according to claim 1,
b) an alkali soluble binder resin,
c) a photopolymerization initiator, and
d) a solvent.

6. The photosensitive composition according to claim 5, wherein Formula 1 is the following Formula 9:

[Formula 9]

in Formula 9,
Z1 to Z4 are the same as or different from each other, and each independently represented by the following Formula 3 or 4,

[Formula 3]

[Formula 4]

A1 to A4 are the same as or different from each other, and each independently an alkylene group having 1 to 6 carbon atoms, and A5 to A8 are the same as or different from each other, and each hydrogen or an alkyl group having 1 to 6 carbon atoms.

7. The photosensitive composition according to claim 6, wherein all of A1 to A4 are a methylene group, and A5 to A8 are the same as or different from each other, and each hydrogen or a methyl group.

8. The photosensitive composition according to claim 5, wherein a) the compound represented by Formula 1 is included in an amount of 5 wt % or more based on the total weight of the solid except for the solvent.

9. The photosensitive composition according to claim 5, wherein the photosensitive composition additionally comprises a crosslinkable compound containing two or more unsaturated groups.

10. The photosensitive composition according to claim 9, wherein the crosslinkable compound containing two or more unsaturated groups is one or two or more selected from the group consisting of compounds obtained by esterifying a polyhydric alcohol with α,β-unsaturated carboxylic acids; compounds obtained by adding (meth)acrylic acids to a glycidyl group-containing compound; ester compounds obtained from a polyhydric carboxylic acid and a compound having a hydroxyl group or an ethylenically unsaturated bond, or polyisocyanate adducts of compounds having a hydroxyl group or an ethylenically unsaturated bond; (meth) acrylic acid alkyl esters; and 9,9'-bis[4-(2-acryloyloxyethoxy)phenyl]fluorene.

11. The photosensitive composition according to claim 5, wherein the photosensitive composition additionally comprises a silica dispersion.

12. The photosensitive composition according to claim 5, wherein b) the alkali soluble binder resin has a weight average molecular weight from 3,000 to 150,000.

13. The photosensitive composition according to claim 5, wherein b) the alkali soluble binder resin has an acid value from 30 KOH mg/g to 300 KOH mg/g.

14. The photosensitive composition according to claim 5, wherein c) the photopolymerization initiator is one or two or more selected from the group consisting of triazine-based compounds; biimidazole compounds; acetophenone-based compounds; O-acyloxime-based compounds; benzophenone-based compounds; tioxanthone-based compounds; phosphine oxide-based compound; and coumarin-based compounds.

15. The photosensitive composition according to claim 5, wherein the photosensitive composition comprises
a) the crosslinkable compound comprising the compound represented by Formula 1 according to claim 1 in an amount from 1 part by weight to 30 parts by weight,
b) the alkali soluble binder resin in an amount from 1 part by weight to 20 parts by weight,
c) the photopolymerization initiator in an amount from 0.1 part by weight to 5 parts by weight, and
d) the solvent from 50 parts by weight to 95 parts by weight, based on 100 parts by weight of the entire composition.

16. The photosensitive composition according to claim 5, wherein the photosensitive composition additionally comprises one or two or more selected from a colorant, a curing accelerator, a thermal polymerization inhibitor, a plasticizer, an adhesive accelerator, a filler, and a surfactant.

17. The photosensitive composition according to claim 16, wherein the colorant is included in an amount from 1 part by weight to 20 parts by weight based on 100 parts by weight of the entire composition.

18. The photosensitive composition according to claim 16, wherein the curing accelerator, the thermal polymerization inhibitor, the plasticizer, the adhesive accelerator, the filler, or the surfactant is included in an amount from 0.01 part by weight to 5 parts by weight based on 100 parts by weight of the entire composition.

19. A photosensitive material prepared by using the photosensitive composition of claim 5.

20. The photosensitive material according to claim 19, wherein the photosensitive material is a photoacrylic photosensitive material, a pigment-dispersion type photosensitive material, a photosensitive material for forming a black matrix, a photosensitive material for forming an overcoat layer or a column spacer photosensitive material.

* * * * *